United States Patent
Mathiaszyk et al.

(10) Patent No.: US 11,896,103 B2
(45) Date of Patent: Feb. 13, 2024

(54) HAIR TREATMENT APPARATUS, HAIR TREATMENT SYSTEM, AND METHOD FOR COSMETICALLY TREATING HAIR

(71) Applicant: Henkel AG & Co. KGaA, Duesseldorf (DE)

(72) Inventors: Carsten Mathiaszyk, Essen (DE); Torsten Lechner, Langenfeld (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 861 days.

(21) Appl. No.: 16/614,143

(22) PCT Filed: May 29, 2018

(86) PCT No.: PCT/EP2018/063993
§ 371 (c)(1),
(2) Date: Nov. 15, 2019

(87) PCT Pub. No.: WO2018/219899
PCT Pub. Date: Dec. 6, 2018

(65) Prior Publication Data
US 2020/0146413 A1  May 14, 2020

(30) Foreign Application Priority Data
Jun. 1, 2017 (DE) ...................... 10 2017 209 339.0

(51) Int. Cl.
*A45D 44/00* (2006.01)
*A61B 5/00* (2006.01)
(Continued)

(52) U.S. Cl.
CPC ............. *A45D 2/001* (2013.01); *A45D 44/00* (2013.01); *A61B 5/448* (2013.01); *A61Q 5/00* (2013.01); *A45D 2044/007* (2013.01)

(58) Field of Classification Search
USPC ......................................................... 132/202
See application file for complete search history.

(56) References Cited

U.S. PATENT DOCUMENTS 5,025,514 A * 6/1991 Miller .................... A45D 19/16
4/518
2012/0227758 A1 9/2012 Ford et al.
(Continued)

FOREIGN PATENT DOCUMENTS

EP 3025611 A1 6/2016
EP 3028596 A1 6/2016

OTHER PUBLICATIONS

EPO, International Search Report and Written Opinion issued in International Application No. PCT/EP2018/063993, dated Aug. 13, 2018.

*Primary Examiner* — Mikhail Itskovich
(74) *Attorney, Agent, or Firm* — Lorenz & Kopf, LLP

(57) ABSTRACT

In various embodiments, a hair treatment device is provided. The hair treatment device has a device body, a first sensor and a second sensor arranged in or on the device body, the first sensor adapted for detecting a hair condition parameter and the second sensor adapted for detecting movements and location changes of the device body. An electronic circuit device is arranged in or on the device body. The electronic circuit device is coupled to the first sensor and the second sensor, and further is configured to control a hair treatment parameter based on the received detected hair condition parameter and/or to dose a hair treatment agent and/or to provide a hair treatment recommendation. The electronic circuit device further is configured to determine a spatial position of the device body and/or a speed of the device body based on the received movements and location changes.

19 Claims, 5 Drawing Sheets

(51) Int. Cl.
*A45D 2/00* (2006.01)
*A61Q 5/00* (2006.01)

(56) References Cited

U.S. PATENT DOCUMENTS

| | | |
|---|---|---|
| 2012/0312320 A1* | 12/2012 | Humphreys ............. A45D 1/28 |
| | | 132/211 |
| 2013/0319450 A1 | 12/2013 | Ragosta et al. |
| 2014/0202487 A1 | 7/2014 | Fereyre et al. |
| 2015/0305468 A1 | 10/2015 | Ragosta et al. |
| 2015/0335120 A1 | 11/2015 | Moore et al. |
| 2015/0342515 A1 | 12/2015 | Hutchings et al. |
| 2016/0058150 A1* | 3/2016 | Yu ............................ A45D 1/28 |
| | | 132/211 |
| 2016/0286927 A1 | 10/2016 | Winkler et al. |
| 2018/0246762 A1* | 8/2018 | Tarsa .................... G06F 9/5083 |
| 2018/0283019 A1* | 10/2018 | Telleria ................... B24B 55/06 |

* cited by examiner

HAIR TREATMENT APPARATUS, HAIR TREATMENT SYSTEM, AND METHOD FOR COSMETICALLY TREATING HAIR

CROSS-REFERENCE TO RELATED APPLICATION

This application is a U.S. National-Stage entry under 35 U.S.C. § 371 based on International Application No. PCT/EP2018/063993, filed May 29, 2018, which was published under PCT Article 21(2) and which claims priority to German Application No. 10 2017 209 339.0, filed Jun. 1, 2017, which are all hereby incorporated in their entirety by reference.

TECHNICAL FIELD

The present disclosure relates to hair cosmetics, in particular a hair treatment device, a hair treatment system and a method for the cosmetic treatment of hair.

BACKGROUND

Users (also referred to as consumers) often do not know to what extent their hair is damaged, and often otherwise know little about the condition of their hair. The hair condition, and especially the degree of hair damage, can vary widely depending on the treatment history and make-up. This information can be important in order to be able to select a correct, that is, for the degree of hair damage, suitable cosmetic hair treatment and/or cosmetic hair treatment agent.

Areas of hair cosmetics include, for example, hair styling, hair care, hair shaping (for example, straightening and/or curling, permanent, semi-permanent, or temporary, wherein temporary hair shaping also is considered to be associated with the hair styling area) and/or hair coloration (also referred to as hair coloring, permanent or temporary).

Hair styling and temporary hair deformation essentially can be based on an effect of hair styling agents. In this case, the hair is usually coated on the surface with a styling agent. This coating causes a change of holding properties of the hair.

The styling products should be adapted to the individual condition of the hair or be selected taking into account the individual condition.

Likewise, care products should be adapted to the individual condition of the hair. Users often use improper care products, that is, not suitable for their hair condition, which make the hair heavy or difficult to handle.

In semi-permanent hair deformation, there is intervention in the hair structure to achieve the cosmetic effect. This is done, for example, by heating the hair by means of a straightening iron or a curling iron. This process may not be harmless to the hair due to the high temperatures (from about 120° C. to about 240° C.) that are acting on the hair. In particular, previously damaged hair can be severely (further) damaged in a misapplied semi-permanent hair deformation, for example, when there is too much (further) heat input by a straightening iron.

The exact coordination of the temperatures used in the straightening and/or cosmetic care products can therefore have an even greater significance in the semi-permanent hair deformation than in the care and temporary hair deformation method described above.

With regard to hair coloring, damaged, already dyed and/or gray hair can often lead to deviations from a desired dyeing result in the case of dyeing (for example, for dyeing's that the user performs himself).

There is thus a need to provide a user with targeted and individual care instructions in the field of hair care, hair styling, hair coloring and/or hair formation.

Furthermore, the user has a need for simpler and less time-consuming cosmetic methods.

In addition, it would be desirable to enable the user to objectively assess treatment success and/or course of treatment during a cosmetic hair treatment. Likewise, it would be desirable to give assistance to the user when performing a cosmetic hair treatment.

BRIEF SUMMARY

In accordance with an exemplary embodiment, a hair treatment device is provided. The hair treatment device comprises, a device body and a first sensor arranged in or on the device body. The first sensor is adapted for detecting a hair condition parameter. The hair treatment device further comprises a second sensor arranged in or on the device body. The second sensor is adapted for detecting movements and location changes of the device body. An electronic circuit device is arranged in or on the device body. The electronic circuit device is coupled to the first sensor for receiving the detected hair condition parameter and the second sensor for receiving the detected movements and locations changes. The electronic circuit device is further configured to control a hair treatment parameter based on the received detected hair condition parameter and/or to dose a hair treatment agent and/or to provide a hair treatment recommendation. The electronic circuit device is further configured to determine a spatial position of the device body and/or speed of the device body based on the received movements and location changes.

In accordance with another exemplary embodiment, a hair treatment system is provided. The hair treatment system comprises a hair treatment device comprising a device body and a first sensor arranged in or on the device body, the first sensor adapted for detecting a hair condition parameter. The hair treatment device further comprises a second sensor arranged in or on the device body, the second sensor adapted for detecting movements and location changes of the device body, and an electronic circuit device arranged in or on the device body. The electronic circuit device is coupled to the first sensor for receiving the detected hair condition parameter and the second sensor for receiving the detected movements and location changes. The hair treatment system further comprises an external data processing device that is adapted to receive from the electronic circuit device the detected hair condition parameter and the detected movements and location changes and to perform, based on the detected hair condition parameter, an action from the group of determining the control or regulation of a detected hair treatment parameter, providing a recommendation for a user, determining a dosing for a hair treatment agent, determining a speed at which hair treatment is to be performed, and a combination thereof. The external data processing device is adapted to transmit the determined control or regulation, the recommendation, the dosing, the speed, or a combination thereof to the electronic circuit device.

In accordance with a further embodiment, a method for cosmetically treating hair is provided. The method comprises the steps of receiving a hair condition parameter produced by a sensor of a hair treatment device and controlling a hair treatment parameter of the hair treatment device based on the hair condition parameter.

BRIEF DESCRIPTION OF THE DRAWINGS

The various embodiments will hereinafter be described in conjunction with the following drawing figures, wherein like numerals denote like elements, and wherein.

DETAILED DESCRIPTION

Figure 1:
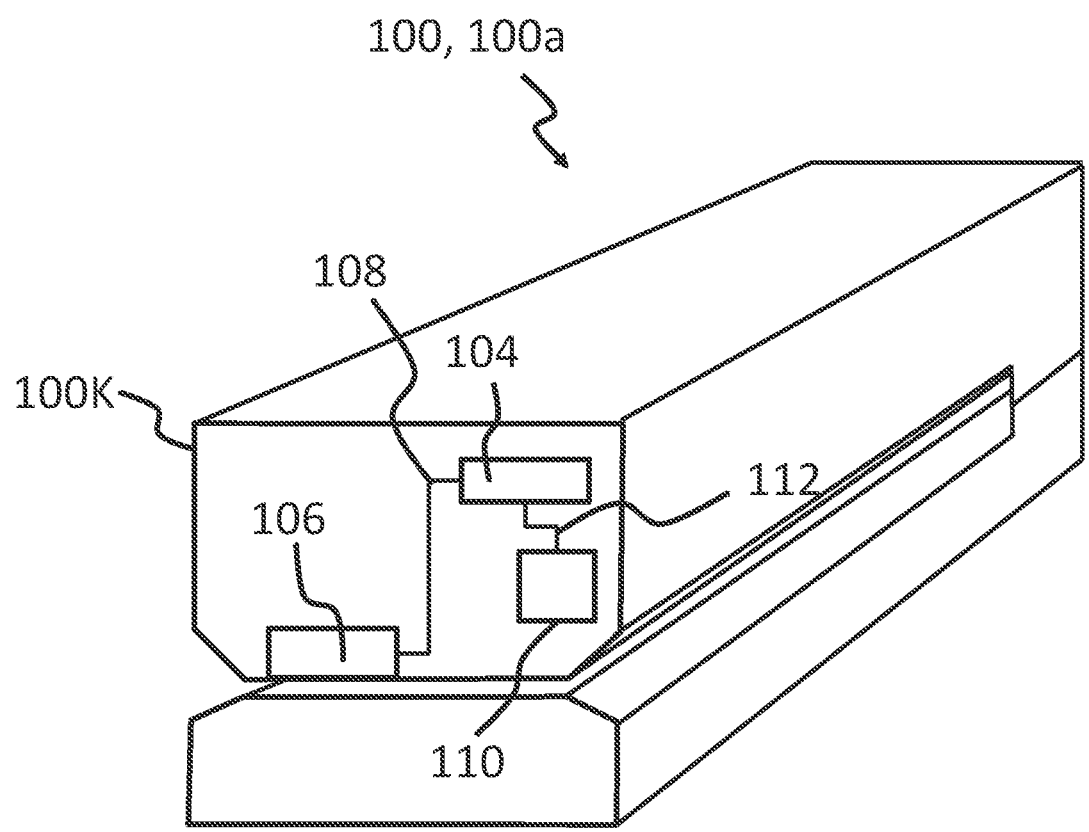
FIG. 1 illustrates a schematic representation of a hair treatment system according to various embodiments.

The following detailed description is merely exemplary in nature and is not intended to limit the disclosure or the application and uses of the subject matter as described herein. Furthermore, there is no intention to be bound by any theory presented in the preceding background or the following detailed description.

In accordance with various embodiments contemplated herein, a hair treatment device is provided which determines a hair condition by means of at least one integrated sensor and, based on the determined hair condition, controls a hair treatment parameter and/or doses at least one hair treatment agent and/or provides a hair treatment recommendation and which determines movements and location changes by means of at least one further integrated sensor and determines a spatial position and/or speed based on the determined movements and location changes. In various embodiments, the hair treatment parameter can be a parameter that is adjustable on the hair treatment device, for example, a temperature of the hair treatment device. In various embodiments, the hair treatment agent can be applied by means of the hair treatment device, for example, on the hair and/or on the scalp, and a dosage, for example, by means of valves, can be carried out by means of the hair treatment device. In various embodiments, the hair treatment recommendation can refer to hair treatment parameters of a hair treatment made by the hair treatment device that are inaccessible to a direct control by the hair treatment device, for example, a recommendation as to which hair treatment agents to fill in tanks of the hair treatment device and/or at what speed hair treatment must be carried out along the hair, or the like.

In various embodiments, a delivery of care and/or styling agents and a heating of the hair can be combined in a method step in a semi-permanent formation of the hair.

Various embodiments provide methods for semi-permanent hair deformation, temporary hair deformation and hair care.

In the field of semi-permanent hair deformation, methods are provided in various embodiments using small power-carrying devices such as straightening irons, curling irons or drying hoods, and the hair treatment devices and hair treatment systems suitable therefor.

In the field of temporary hair deformation and hair care, methods are provided in various embodiments using small power-carrying devices such as combs or brushes, and the hair treatment devices and hair treatment systems suitable therefor.

In various embodiments, methods are provided which use a combination of a styling device (for example, comb, brush, curling iron, drying hood, in particular straightening iron), a sensor, that is, at least one sensor, wherein the at least one sensor can be integrated or not integrated into the styling device, a processor and an actuator.

Further, hair treatment devices and hair treatment systems are provided which have a combination of a styling device (for example, comb, brush, curling iron, drying hood, in particular straightening iron), a sensor, that is, at least one sensor, wherein the at least one sensor can be integrated or not integrated into the styling device, a processor and an actuator.

In various embodiments, the processor is configured to receive sensor data from the sensor, to evaluate the sensor data and, possibly, to compare the evaluated sensor data with at least one external database (for example, by a cloud).

In various embodiments, the processor further is configured to derive handling instructions from the evaluated sensor data (for example, a method profile including temperature and/or used care and/or styling agents).

In various embodiments, the processor is further configured to transmit handling instructions to the actuator, wherein the actuator can be part of the hair treatment device or the hair treatment system.

In various embodiments, the actuator implements the handling instruction provided by the processor. A handling executed by the actuator has an optical effect in various embodiments (for example, as a warning light, image, diagram, pictogram, on a screen, for example, the screen of a smartphone, film shown, or the like). In various embodiments, the handling executed by the actuator has a mechanical effect (for example, as automatic temperature adjustment and/or automatic dosing adjustment on the styling device and/or a vibration). In various embodiments, the handling executed by the actuator has an acoustic effect (for example, as a warning tone, voice output, or the like).

In various embodiments, the sensor for detecting a hair condition parameter has a hair damage sensor. The hair damage sensor is configured in various embodiments to determine, by means of near-infrared spectroscopy and/or fluorescence spectroscopy, a content of oxidative and/or chemical degradation products of hair ingredients, in particular a cysteic acid content of the hair and to determine therefrom a degree of hair damage. The hair damage sensor is configured in various embodiments to record acoustic emissions detected during combing of the hair, and to determine the degree of hair damage of the hair therefrom, possibly with the aid of the processor.

In various embodiments, the hair damage sensor has a microscopic photosensor. The microscopic photosensor can be configured to detect a hair surface roughness or to enable the determination of hair surface roughness.

In various embodiments, the sensor for detecting a hair condition parameter has a hair thickness sensor. The hair thickness sensor is configured in various embodiments to determine a hair thickness by means of a light sensor. For example, when determining the hair thickness, one can consider that thicker hair absorbs more light. In various embodiments, the hair thickness sensor is configured such that a predetermined amount of hair, for example, single-layer, can be introduced into a given volume and the volume is irradiated by light with a predetermined intensity, wherein the amount of light that reaches the sensor for detecting a hair condition parameter after penetrating the hair can be measured by means of the sensor. The hair thickness can be determined on the basis of the detected light by means of the hair thickness sensor, possibly in conjunction with the processor. In various embodiments, the hair thickness sensor, for example, in a case where the hair thickness sensor has a color camera, also is used for determining a hair color and/or a gray component, possibly with the aid of the processor.

The hair thickness sensor has an ultrasound sensor in various embodiments. The ultrasonic sensor can be configured to emit ultrasonic waves in the direction of the hair, to detect ultrasonic waves reflected by the hair and, therefrom, possibly in conjunction with the processor, to determine the hair thickness.

In various embodiments, the at least one sensor for detecting a hair condition parameter has a hair length sensor. For example, the hair length sensor can have at least one position sensor which makes it possible to determine a distance covered in the hair. In various embodiments, the hair length sensor is combined with a sensor for calculating combability of the hair (see below).

In various embodiments, the hair length is provided by the user instead of determining the hair length by means of the hair length sensor. For example, the user can measure the hair length himself and provide the measured hair length value to the hair treatment device or the hair treatment system.

In various embodiments, the hair thickness sensor has a photo-optical sensor in which an image of at least one hair is recorded.

In various embodiments, the hair thickness sensor has a thermal sensor.

In various embodiments, the at least one sensor for detecting a hair condition parameter has a gray component sensor. From the at least one gray component sensor, an image of the hair can be recorded by an optical sensor, for example, by a camera. To determine the gray component in the hair, the image can be compared in various embodiments with at least one existing image, for example, a reference image, which can be stored, for example, internally and/or externally, in order to determine the gray component.

In various embodiments, the sensor for detecting a hair condition parameter has a straightness/curl sensor that can be configured to determine a hair structure in the sense of straight hair to curly or frizzy hair. The straightness/curl sensor has a camera in various embodiments. The straightness/curl sensor is configured in various embodiments, possibly in conjunction with the processor, for example, by an image processing program, to determine a straightness or curl of the hair.

In various embodiments, the sensor for detecting a hair condition parameter has a hair moisture sensor. The hair moisture sensor is configured in various embodiments to determine a water content of the hair. The hair moisture sensor can, for example, be designed as a near-infrared spectroscope, which can be configured to examine near-infrared (NIR) absorption structures of water and, based on this, possibly with the aid of the processor, to determine the hair moisture.

In various embodiments, the at least one sensor for detecting a hair condition parameter has a combability sensor. The combability sensor can be configured to detect a force (for example, by means of strain gauges), which is used in combing the hair.

In various embodiments, the at least one sensor for detecting a hair condition parameter has a hair density sensor. The hair density sensor can have, for example, a camera or a camera attachment which can be configured to be held directly to a region of the hair root, for example, to be placed directly on a scalp. A hair density can be based on the image, for example, based on a number of hairs and/or a distance between the hairs, to determine the hair density.

In various embodiments, the sensor for detecting a hair condition parameter is configured to determine further hair condition parameters.

In various embodiments, the sensor for detecting a hair condition parameter, for example, in the case of a spectrometer or a camera, is configured to determine several hair condition parameters, for example, both the degree of hair damage based on the cysteic acid absorption structures in the NIR spectrum and the hair moisture based on the water absorption structures in the NIR spectrum.

In various embodiments, the hair treatment device or the hair treatment system has or is a heatable device. That is, in various embodiments, the hair treatment device or the hair treatment system has a heating device. The heating device is controlled or regulated in various embodiments depending on the result of the hair analysis (damage, hair thickness, curl, water content). For example, for more intact, thicker, curlier and/or wetter hair, the hair treatment device or hair treatment system can be controlled or regulated to treat the hair at a higher temperature than when the hair is damaged, thinner, straighter and/or drier.

In various embodiments, the hair treatment device and/or the hair treatment system has a straightening iron, a curling iron and/or a drying hood with a temperature control and/or a temperature regulation.

In various embodiments, the hair treatment device and/or the hair treatment system has a straightening iron, a curling iron and/or a drying hood with a (for example, refillable) tank for receiving and dosed delivery of a hair treatment agent (also referred to as active substance tank) and a dosing device.

In various embodiments, the hair treatment device and/or the hair treatment system has a comb and/or a brush with a (for example, refillable) tank for receiving and dosed delivery of a hair treatment agent and a dosing device.

In various embodiments, the hair treatment device and/or the hair treatment system, for example, the styling device, has the sensors in a double design. In this case, a plurality of (for example, similar) sensors can be arranged such that the user can immediately receive feedback on whether further treatment (also referred to as "post-treatment") is necessary. In various embodiments, the hair treatment device and/or the hair treatment system, for example, the styling device, has sensors on both sides of the heating device, wherein a sensor for detecting a hair condition parameter measures a hair condition parameter before and a sensor for detecting a hair condition parameter measures a hair condition parameter (for example, the same) after the temperature treatment of the hair.

In various embodiments, the hair treatment device and/or the hair treatment system, for example, the styling device, alternatively or additionally has a dispensing device. A hair treatment agent, such as a care or styling agent, can be located in the delivery device. Depending on the result of the hair analysis (damage, hair thickness, curl, water content), the hair treatment agent, which can have, for example, a (for example, chemical) composition, optionally in different volumes/amounts depending on the position [hair line, middle, tips], can be applied to the hair.

In various embodiments, by use of the hair treatment device and/or the hair treatment system, two or more agents in different mixing ratios depending on position [hair line, middle, tips] or at different positions are applied to the hair.

In various embodiments, the hair treatment device and/or the hair treatment system has a dispensing device that can have pumps for dispensing the agent, which can be or are controlled, for example, by wireless instructions (for example, instructions transmitted by means of WLAN, Bluetooth, or the like), which can be sent by the processor. For example, a flow rate of the agent(s) can be adjusted.

In various embodiments, a user receives information about a condition of his hair (also referred to as hair status).

In various embodiments, a user receives a personalized cosmetic treatment and/or treatment recommendation adapted to his hair status.

In various embodiments, a user already receives information about a course of the application while performing a hair treatment. A hair treatment result can still be optimized while performing the hair treatment so that frustration can be avoided.

In various embodiments, a time-saving hair treatment method is provided, for example, by performing a (temporary, semi-permanent or permanent) hair forming treatment at least in part together with a hair care treatment.

In various embodiments, a hair treatment device is provided in the form of a straightening iron, in which at least one sensor for detecting a hair condition parameter, is integrated into the straightening iron, an electronic circuit device, which can have a processor, is integrated into the straightening iron, and a first actuator which can, for example, have a temperature control or a temperature regulation, which controls or regulates a temperature of heatable surfaces of the straightening iron, is integrated into the straightening iron. In addition, in various embodiments, the straightening iron has a second actuator, which can have, for example, a dosing device for a hair care and/or hair styling agent.

In various embodiments, a hair treatment system is provided in the form of a straightening iron in which at least one sensor for detecting a hair condition parameter is part of a first separate communication capable device (that is, a data exchange device) (for example, a smartphone having a camera, a spectrometer with the data exchange device or a so-called "acoustic comb", which can be configured to detect noise generated during combing), an electronic circuit device, which can have a processor, is integrated in the straightening iron, and a first actuator which, for example, can have a temperature control or a temperature regulation, which controls or regulates a temperature of heated surfaces of the straightening iron, is integrated in the straightening iron. In addition, in various embodiments, the straightening iron has a second actuator, which can have, for example, a dosing device for a hair care and/or hair styling agent. In various embodiments, the straightening iron has a data exchange device, for example, for receiving measured values detected by at least one sensor.

In various embodiments, a hair treatment system is provided in the form of a straightening iron, in which at least one sensor for detecting a hair condition parameter is part of a first separate communication capable device (that is, having a data exchange device) (for example, a smartphone having a camera, a spectrometer with the data exchange device, or a so-called "acoustic comb" that can be configured to detect noise generated during combing), an electronic circuit device, which can have a processor, is integrated into the first separate communication capable device, and a first actuator, which can have, for example, a temperature control or a temperature regulation that controls or regulates a temperature of heatable surfaces of the straightening iron, is integrated into the straightening iron. In addition, in various embodiments, the straightening iron has a second actuator, which can have, for example, a dosing device for a hair care and/or hair styling agent. In various embodiments, the straightening iron has a data exchange device, for example, for receiving recommendations and/or control instructions determined by means of the electronic circuit device.

In various embodiments, a hair treatment system is provided in the form of a straightening iron, in which at least one sensor for detecting a hair condition parameter is integrated into the straightening iron, an electronic circuit device, which can have a processor, is part of a second separate communication capable (that is, having a data exchange device) (for example, part of a smartphone on which, for example, an app can be installed, or, for example, a cloud or the like), and a first actuator, which can, for example, have a temperature control or a temperature regulation, which controls or regulates a temperature of heatable surfaces of the straightening iron, is integrated into the straightening iron. In addition, in various embodiments, the straightening iron has a second actuator, which can have, for example, a dosing device for a hair care and/or hair styling agent. In various embodiments, the straightening iron has a data exchange device, for example, for receiving recommendations and/or control instructions determined by the electronic circuit device.

In various embodiments, a hair treatment system is provided in the form of a straightening iron, in which at least one sensor for detecting a hair condition parameter is part of a first separate communication capable device (that is, having a data exchange device) (for example, a smartphone having a camera, a spectrometer with the data exchange device, or a so-called "acoustic comb" that can be configured to determine noise generated during combing), an electronic circuit device, which can have a processor, is part of a second separate communication capable device (that is, having a data exchange device) (for example, part of a smartphone on which, for example, an app can be installed, or for example, a cloud or the like), and a first actuator, which can have, for example, a temperature control or a temperature regulation that can control or regulate a temperature of heatable surfaces of the straightening iron, is integrated into the straightening iron. In addition, in various embodiments, the straightening iron can have a second actuator, which can have, for example, a dosing device for a hair care and/or hair styling agent. In various embodiments, the straightening iron has a data exchange device, for example, for receiving recommendations and/or control instructions determined by the electronic circuit device.

In various embodiments, a hair treatment device is provided in the form of a comb, in which at least one sensor for detecting a hair condition parameter (for example, in the form of a microphone or a camera for detecting hair condition parameters) is integrated into the comb, an electronic circuit device, which can have a processor, is integrated into the comb, wherein the processor can be configured to determine by the detected hair condition parameters, for example, a degree of hair damage and based thereon, to determine at least one control parameter and possibly at least one recommendation, and a first actuator that can, for example, have a dosing device for a hair care and/or hair styling agent, is integrated into the comb or is connectable with the comb to an integrated system, for example, in the form of an attachment for the comb.

In various embodiments, a hair treatment system is provided in the form of a comb, in which at least one sensor for detecting a hair condition parameter is part of a first separate communication capable device (that is, having a data exchange device) (for example, a smartphone having a camera, a spectrometer with the data exchange device, or a so-called "acoustic comb"), an electronic circuit device, which can have a processor, is integrated into the comb, wherein the processor can be configured to determine, by the detected hair condition parameters, for example, a degree of hair damage and based thereon, to determine at least one control parameter and possibly at least one recommendation, and a first actuator, which can have, for example, a dosing device for a hair care and/or hair styling agent, is integrated into the comb or is connectable with the comb to an integrated system, for example, in the form of an attachment for the comb. In various embodiments, the comb can have a data exchange device, for example, for receiving recommendations and/or control instructions determined by the electronic circuit device.

In various embodiments, a hair treatment system is provided in the form of a comb, in which at least one sensor for detecting a hair condition parameter is part of a first separate communication capable device (that is, having a data exchange device) (for example, a smartphone having a camera, a spectrometer with the data exchange device, or a so-called "acoustic comb"), an electronic circuit device, which can have a processor, is integrated into the first separate communication capable device, and a first actuator, which can have, for example, a dosing device for a hair care and/or hair styling agent, is integrated into the comb or is connectable with the comb to an integrated system, for example, in the form of an attachment for the comb. In various embodiments, the comb can have a data exchange device, for example, for receiving recommendations and/or control instructions determined by the electronic circuit device.

In various embodiments, a hair treatment system is provided in the form of a comb, in which at least one sensor for detecting a hair condition parameter is integrated into the comb, an electronic circuit device, which can have a processor, is part of a second separate communication capable device (that is, having a data exchange device) (for example, part of a smartphone, on which an app can be installed, or for example, a cloud or the like), and a first actuator, which can, for example, have a dosing device for a hair care and/or hair styling agent, is integrated into the comb or is connectable with the comb to an integrated system, for example, in the form of an attachment for the comb. In various embodiments, the comb has a data exchange device, for example, for receiving recommendations and/or control instructions determined by the electronic circuit device.

In various embodiments, a hair treatment system is provided in the form of a comb in which at least one sensor for detecting a hair condition parameter is part of a first separate communication capable device (that is, a data exchange device) (for example, a smartphone having a camera, a spectrometer with the data exchange device, a so-called "acoustic comb"), an electronic circuit device, which can have a processor, is part of a second separate communication capable device (that is, having a data exchange device) (for example, part of a smartphone on which, for example, an app can be installed, or, for example, a cloud or the like), and a first actuator, which can, for example, have a dosing device for a hair care and/or hair styling agent, is integrated into the comb or is connectable with the comb to an integrated system, for example, in the form of an attachment for the comb. In various embodiments, the comb has a data exchange device, for example, for receiving recommendations and/or control instructions determined by means of the electronic circuit device.

In various embodiments, a hair treatment system is provided, which has a hair treatment device (for example, a straightening iron, a curling iron, a comb, a brush, or the like), and further, a hair condition determination device that can be configured to detect a degree of hair damage, for example, by at least one sensor integrated into the hair condition determination device (the hair condition detection device can, for example, have a comb equipped with sensors or an NIR camera or an NIR spectrometer or a UV spectrometer or a UV/VIS spectrometer or a VIS/NIR spectrometer, which can be suitable for determining a hair condition parameter, for example, a hair structure). Via a smartphone app that can act as the heart of the system, targeted information, such as control or regulation instructions, can be then transmitted to the hair treatment device (for example, a "smart" straightening iron), which can be configured, based on the control or regulation instructions, to control or regulate a hair treatment parameter and/or to dose a hair treatment agent (in the case of the straightening iron, for example, a temperature can be adjusted, with which the hair can be treated without further damage). A data exchange can be made wirelessly, for example, via Bluetooth, WLAN or near field communication technology (NFC technology).

In various embodiments, a hair treatment system is provided, which has a hair treatment device (for example, a straightening iron, a curling iron, a comb, a brush, or the like), and further has a data connection (the term connectivity is also used for the option of data exchange) between an external app and the hair treatment device (for example, a hair care/styling device). In various embodiments, care/styling parameters can be provided, for example, predetermined (in a case where the hair treatment device has the straightening iron or curling iron, the parameter can, for example, have a maximum temperature), wherein the parameter provided can be related to a degree of damage of the hair, that is, depending on the degree of damage of the hair, the parameter can have a different value.

In various embodiments, a temperature of a straightening iron can be controlled or regulated, taking into account a degree of damage of the hair.

In various embodiments, a "smart" styling device (for example, a comb, a brush, a curling iron, a straightening iron, or the like) and/or a "smart" terminal (for example, a smartphone, a tablet, a smart mirror, or the like) has a sensor for detecting a hair condition parameter, which sensor can be integrated in the styling device and/or the terminal and/or designed as a removable attachment and/or as a separate portable device. The styling device and/or the terminal can be configured to detect one or more hair condition parameters, for example, hair characteristics. The detected data can be evaluated by the styling device and/or the terminal, for example, by an app and/or a program that can be installed on the styling device and/or the terminal, and a (personalized) recommendation can be provided to the user, for example, in the form of so-called DOs (recommendations) and DON'Ts (warnings). An example of this would be "Take or do not take a waxy product". In various embodiments, the providing of the recommendation can be made optically, for example, by means of a display device, for example, by means of a display. In various embodiments, the providing of the recommendation alternatively or additionally is made acoustically, for example, as a voice output. In various embodiments, the providing of the recommendation is made by the styling device and/or by the terminal.

In various embodiments, the hair treatment device or the hair treatment system has an input device. The input device can be configured to receive at least one input by the user and to provide it to the electronic circuit device and/or an external data processing device. Parameters to be input by the user can have, for example, a desired hair color, a desired treatment (for example, hair formation, styling, care), a hair length, a hair curl (for example, comparative images can be provided for an input) or the like.

In an embodiment, the hair treatment device further has at least one sensor arranged in or on the device body for detecting movements and location changes of the device body.

With the aid of the electronic circuit device arranged in or on the device body, which is coupled to the at least one sensor for detecting movements and location changes of the device body and which receives the detected sensor data, a spatial position of the device body and/or the speed of the device body is determined based on the received detected sensor data.

In various embodiments, the electronic circuit device further determines whether the determined speed of the device body meets a predetermined criterion according to a provided speed for applying the hair treatment device.

In an embodiment, the electronic circuit device is configured to deliver a signal depending on whether the determined speed meets the predetermined criterion. The signal can comprise an acoustic signal, an optical signal and/or a haptic signal. For example, when the hair treatment device is moved too slowly through the hair, the user can be notified by a sound signal, a light signal or a vibration of a part of the hair treatment device, for example, a handle.

In various embodiments, the delivery of the signal, during the application of the hair treatment device, preferably takes place with a response time of less than about 1 second for detecting the sensor data relating to the movements and location changes of the device body.

In various embodiments, based on the determined spatial position of the device body, the electronic circuit device determines which hair regions have already been treated with the hair treatment device and transmits the determined hair regions to a display device, which is preferably a component of a computer, a smartphone, a tablet, a smart mirror, a smart watch or a laptop. A data exchange can be made wirelessly, for example, via Bluetooth, WLAN, ZigBee, Thread or near field communication technology (NFC technology).

The determined, already treated hair regions can be displayed on the display device in a representation of the user (for example, a schematic representation or on a photo of the user). For example, regions already treated with the hair treatment device and untreated regions can be represented with different colors and/or patterns in a schematic representation of the hairstyle of the user, for example, already treated regions green and untreated regions red or the like. In another example, a user's photograph, for example, a digital photograph showing the user's hair or hairstyle, can be overlaid with different patterns, for example, a dot pattern for regions already treated and a line pattern for untreated regions, or similar. Alternatively, the real-time representation of a user on/in a smart mirror can be used to display the already treated and/or untreated hair regions.

In various embodiments, the sensor for detecting movements and location changes of the device body is selected from the group including magnetic field sensors, gyroscopes, acceleration sensors, and mechanical displacement sensors. In a particularly preferred embodiment, the sensor for detecting movements and location changes of the device body is a gyroscope.

Alternatively or additionally, the determination of the spatial position of the hair treatment device and the determination of the previously treated hair regions takes place with the aid of an app or a program that is installed on a separate data processing device. In this case, the electronic circuit device transmits the detected sensor data for movement and location change of the device body, preferably wirelessly, to the separate data processing device. In the case where the separate data processing device comprises a display device, the representation of the hair regions already treated with the hair treatment device and/or untreated can take place with the aid of the display device of the separate data processing device.

The sensor for detecting movements and location changes can also be a component of a hair treatment system. In this embodiment, for example, the sensor for detecting movements and location changes, for example, is part of a first separate communication capable device. It is particularly preferred that, when using a hair treatment system in the form of a straightening iron or a comb, the sensor for detecting movements and location changes is integrated in the straightening iron or comb.

In various embodiments, the hair treatment device, for example, the smart styling device, further has a dispensing device. For example, a hair treatment agent can be arranged in at least one tank in the dispensing device in various embodiments, for example, a hair care agent, a hair styling agent or a hair coloring agent. In various embodiments, depending on the determined at least one hair condition parameter (which can be a result of a hair analysis performed based on the sensor data), the hair treatment agent can be applied in different volumes or amounts depending on the position (for example, hair line/middle/tips), for example, a different volume/amount on the hair tips than on the hairline. Alternatively or additionally, two or more hair treatment compositions in different mixing ratios can be applied to the hair, depending on the position (for example, hairline/middle/tips) or at different hair sites (for example, as an ombré coloring). The dispensing device can have at least one pump for dispensing the hair treatment agent. The at least one pump can be controlled or regulated, for example, by a smartphone or the like, for example, by an app. For example, a flow rate of the hair treatment agent can be adjusted by the smartphone.

In various embodiments, the dispensing device is separate from the hair treatment device.

The dispensing device, in various embodiments, is controlled by a wireless transmission device, for example, by the dispensing device receiving control commands by the wireless transmission device. The wireless transmission device can be part of the electronic circuit device, for example. The wireless transmission device, in various embodiments, has a chip or tag which enables the wireless data transmission, for example, by means of Bluetooth, WLAN (WiFi), Zigbee, NFC, Wibree, Thread, WiMAX or the like.

In various embodiments, providing the recommendation to the user includes providing by transmitting the recommendation to a display device and displaying the recommendation.

The transmission can be done in various embodiments by a wireless transmission device. The wireless transmission device can be part of the electronic circuit device, for example. The wireless transmission device, in various embodiments, has a chip or tag that enables the wireless data transmission, for example, by Bluetooth, WLAN (WiFi), Zigbee, NFC, Wibree, Thread, WiMAX or the like.

In various embodiments, prior to providing a recommendation to the user, a data comparison is made between the smart terminal and/or the smart styling device and data, for example, reference data, which can be stored, for example, in a cloud. In various embodiments, the data has data from other users having, for example, the same at least one hair condition parameter, and, for example, corresponding derived recommendations/measures.

In various embodiments, a user already receives information about a course of the application while performing a hair treatment. This can make it possible to already optimize a hair treatment result during the performance. This can avoid frustration for the user.

In various embodiments, a user obtains information about a hair condition, that is, a status of the hair, which enables (for example, direct) instructions to be generated, for example, an instruction as to when a dyeing process must be finished (for example, by timely rinsing of the hair, to avoid a dark dyeing result).

In various embodiments, the recommendation for care and styling products and/or the use instructions refer to a chemical composition of the recommended and not recommended care, and styling products, for example, in the form of so-called DOs (recommendations) and DON'Ts (warnings). An example of this would be "Take or do not take a waxy product".

Depending on the hair thickness and hair density, the user is given a recommendation on a suitable styling product, in various embodiments. For example, it can be disadvantageous to use a styling wax on thin, light hair, as this will quickly cause greasiness and unkemptness in such a hair type. The category "wax" includes products that are distinguished by a high proportion of wax components, vaselines, emulsifiers and oils or oily or oil-containing components. Also not recommended for thin light hair can be emulsions, which can also be exemplified by a high proportion of just-described raw materials.

Depending on the nature of the ingredients used in the hair care and/or hair styling products, the use of these ingredients in a determined hair type can be recommended to the user or can be discouraged from use.

Depending on the curl condition (curls or rather waves), the user is advised, in various embodiments, that a product either supports his natural curl image, or in the case of waves also strengthens (also known as pushing) and stabilizes. Certain polymers, such as Styleze CC10 (VP/DMAPA Acrylates Copolymer), and Mirustyle CP (Polyquaternium-72), can be particularly helpful here. However, standard polymers, such as PVP, PVP/VA, etc., and/or further polymers whose curl-holding or generation properties are known to those skilled in the art at the time of publication, can well be suitable for holding the curls.

Curls usually require a lot of care, so that even with curly hair, a nourishing emulsion/lotion can be beneficial. Furthermore, mousses can be applied to support bounce and springiness and to define the curls. In various embodiments, the polymers mentioned above for curl definition are used. The curl definition can also be achieved with a light wax, whereas a (heavy) wax acts more as a drag on waves and probably cannot help the consumer to maintain his styling result over a longer time period. However, in various embodiments, additional support also is provided here by polymers (for example, as mentioned above) in order to prolong the result and the holding power.

Even with long hair, an application of a wax or gel can be unusual in various embodiments. In this case, the user can be advised to fall back to lighter consistencies, such as blow-dry sprays, mousses, lotions or the like, in order to support their look. Particularly sprayable or low-viscosity pumpable products can be well suited here, since they can be distributed particularly easily over the entire hair length. Depending on the desired styling effect, there can also be polymer types that can be used (for example, PVP, PVP/VA, Chitosan, Polyquaternium types, etc.).

In various embodiments, a choice of the right product usually is related to the desired styling result. Thus, for example, a blow-dry spray or a mousse can be provided to aid in blow-drying, and can also contain nourishing styling components that allow working with comb and brush in wet hair (for example, Polyquaternium-4, Polyquaternium-11, Polyquaternium-46, etc., Chitosan, Polyacrylamidopropyltrimonium Chlorides, etc.).

A hairspray can be provided to fix the final hairstyle and also to protect against external influences endangering the hairstyle. An example of such an external influence would be the influence of high air humidity. Certain polymers can counteract this, for example, amphomer (see table).

Short, strong hair can be well shaped and kept in shape with gels, waxes, pastes, creams and hair sprays (see table).

The longer the hair, the stronger the desire of the user to remove the styling product from the hair before going to bed. Short hair which has been styled with waxes, pastes, creams, gels or the like can usually wash out quickly with water and dry quickly afterwards (possibly by using a hair dryer). Longer hair styled with a styling mousse and/or fixed with a hairspray is often brushed off. For this purpose, it can be helpful when the applied fixing polymer is easily brittle and fragile and can be removed, for example, by using a comb/a brush. Said polymers would be, for example, PVP, PVP/VA, amphomer, etc. (see table).

Users with African-American hair can prefer products that have one thing in common: much care. This target group can feel that their hair is very dry and brittle and needs much moisture. In particular, rich, creamy textures can be desirable here, and also oil sprays that make the hairstyle of the user look healthy and well-groomed. Conditioning polymers can help keep the hair in shape without making it stiff and inflexible. Rich waxes and emulsions can provide additional care to the hair and can easily weigh down the hair, so that the hair does not fly (anti-frizz). What would thus be a "no go" on European hair, cannot be nurturing/weighing/greasy enough for African-American hair.

Users with damaged, for example, bleached, hair can need more care in their products than people with healthy ("virgin") hair.

In various embodiments, in addition to the chemical properties, physical properties of the recommended and not recommended care and styling products (DOs and DON'Ts, for example, viscosities, evaporation properties, stickiness) can be crucial or influential as to whether a product is considered as recommended or not for a given hair type.

The longer the hair, the lower the stickiness of formulations should be. Users with long hair especially often want a styling product that holds and styles, but does not stick very hard. Many of them can prefer a natural hair feel and appearance.

In addition to mousses and light sprays or emulsions for blow-drying, long-haired women can often use hairspray to fix their hairstyle. Again, a non-strong adhesive product can be preferred. In addition, however, it can be desirable for the hairspray to be finely dispersed on the hair to avoid the said effect (a concreted/unnatural looking hairstyle).

Even users with curls can care about supporting the curls and making them look natural, and not cement their look.

The thicker and shorter the hair, the higher the product viscosity can be, since it often helps to shape the hair when styling. Here, as already described above, pastes, creams, gels with a high viscosity are suitable.

In various embodiments, in addition to the chemical properties and/or the physical properties, a making-up (also referred to as application form, etc.) of the recommended and not recommended care and styling products (DOs and DON'Ts, for example, spray rather than gel) can be decisive or influential on whether or not a product is considered to be recommended for a given hair type. This is partly described above.

In various embodiments, the determined recommendation are used to make an optimal/personalized styling product, for example, as an order to make an optimal/personalized styling product.

This can be initiated, for example, by calling a manufacturer's website for optimal/personalized hair treatment products, such as styling products.

The optimal/personalized hair treatment product can be a product specially made for the customer or a so-called mass customized product. In the case of a "mass customized" product, an individualization can be achieved by varying a few characteristics of a product that are decisive from the customer's point of view. Preferably, these "mass customized" products are based on the concept of modularization, that is, the product can be assembled individually from various modules/building blocks.

Often, there are many dependencies between the many different features/ingredients of a product, which can be expressed as "commandments" or "prohibitions." In order to obtain a clear product definition, it can be advantageous for the ordering process to proceed with the aid of a product configurator. This configurator helps the customer to select the characteristics/ingredients and draws attention to the permitted/inadmissible combinations of features, wherein the latter then cannot be selected.

With the help of a product configurator, for example, the selection of chemically and/or physically incompatible ingredients or the selection of the ingredients unsuitable for the determined hair condition can be avoided. Conversely, the selection of suitable ingredients for the determined hair condition can be predetermined or suggested by the product configurator.

In various alternative embodiments, a user input is utilized on a delivery device for the optimized delivery of hair treatment product. This delivery device can preferably be present at a hairdresser or at a point of sale (POS) of hair treatment agents. The user can select his hair condition and, possibly, the desired amount of product using a digital display and a touchscreen. For this purpose, a stored recommendation can already be programmed in the device, for example, stored in a database. Such recommendations can be known from leaflets of hair colorations, on which it can frequently be noted that, for example, two coloration packages should be used for shoulder-length hair. A (quantity and) product recommendation can be made by means of a previous individual input of the hair length of the user. This can either be confirmed, extended or reduced by the user when, for example, he already knows that he tends to use more/less product than is normally stated on packaging.

In various embodiments, a method for the cosmetic treatment of hair is provided that allows a correct, that is, suitable for the degree of hair damage, product selection. For example, in the hair treatment, an exact matching product can be used for hair coloring, bleaching, perming, hair care and/or hair styling given its degree of hair damage.

In various embodiments, a user himself determines his degree of hair damage and/or other hair condition parameters for a corresponding evaluation, for example, without performing elaborate microscopy and/or having background knowledge. Thus, the user can be enabled to dispense with expert assistance in determining his hair condition.

Herein, reference can be made to "the sensors", for example, regarding data transmission between the sensors and a data processing device, an arrangement of sensors, etc. It is to be understood that the sensors can have a totality of sensors arranged in the hair treatment device or the hair treatment system, for example, a totality of camera(s), temperature sensor(s), microphone(s), etc., or, if this is evident from the context, a part of said sensors.

In various embodiments, the hair treatment system has an electronic device, for example, a mobile electronic device (also referred to as a mobile device), for example, a smartphone or a tablet, or for example, another data processing device (for example, a PC). In various embodiments, the hair treatment system also uses an (optionally further) external data processing device, for example, a cloud, for signal evaluation, for example, as an extension of the signal evaluation. For this purpose, in various embodiments, the signals detected by the sensors are compared with signals stored in a database (also referred to as comparison signals, comparison data, reference signals or reference data). In various embodiments, the degree of hair damage or another hair condition parameter is classified based on this, for example, by assigning degrees of hair damage to the comparison signals, and assigning the degree of hair damage or the other hair condition parameters of the comparison signal most similar to the measured signal to the measured hair.

In various embodiments, the reference data, which, for example, can be provided as a database, is obtained empirically (for example, in the laboratory) for hair whose degree of hair damage degree can be known. In various embodiments, further information about the hair is present, which serves as a basis for the reference spectra, for example, "hair bleached four times—high degree of damage" or "untreated hair—no damage", and/or for the hair which is used to determine the reference spectra, a development of a hair condition, for example, the degree of hair damage can be provided, for example, several reference spectra, each of which was taken after a different hair treatment step, wherein the hair treatment can have a nourishing hair treatment and/or a damaging hair treatment. An agent (for example, product and/or ingredient) used in a treatment can also be detected by the database.

In various embodiments, a user also is provided with the additional information (for example, the database), for example, which degree of treatment corresponds to his hair condition, and/or how his hair condition is likely to develop when he performs a particular treatment, for example, applies a particular agent.

In various embodiments, for example, when using a cloud, the database alternatively is generated (for example, continuously supplemented) in the laboratory by user data. In various embodiments, the database generated in the laboratory is supplemented by user data that can be provided by means of the cloud.

In various embodiments, the hair treatment device is provided as an accessory, for example, a "smart accessory" for a smartphone (or similar device such as a tablet, an iPod, or the like), which can be connected to the smartphone, for example, plugged therein, whereby processing capabilities and/or sensors of the smartphone can be enabled. In various embodiments, the hair treatment system has such an accessory.

In various embodiments, the hair treatment system is provided as a stand-alone device, which can have, for example, its own device for transmitting data and thus can be a so-called "Internet of Things (IoT)" device. The stand-alone hair treatment device can transmit the recorded data (for example, acoustic data and possibly speed data) to an external data processing device, for example, to a cloud, for example, by Bluetooth, WLAN (WiFi), NFC or the like.

In various embodiments, the recorded data, as described elsewhere herein, is analyzed by software algorithms to determine a hair conditional parameter, for example, a degree of hair damage.

In various embodiments, for example, when the reference data are provided by the cloud, these are available to a user at any time in order to be used as reference data for a comparison.

In various embodiments, the data detected by the hair treatment device or by the hair treatment system is stored, for example, in a memory integrated into the hair treatment device and/or into the external data processing device, for example, the cloud. The stored data can be stored so that at least the user is enabled to recognize this data as his data. This makes it possible to compare hair information obtained, for example, at different points in time (for example, before and after a treatment) with each other.

In various embodiments, the hair treatment device and/or the hair treatment system has a connection for transmitting data, for example, between a smartphone/tablet, which can be part of the hair treatment system, and a cloud, and/or between the hair treatment device and a smartphone/tablet, and/or between a hair treatment device and a cloud.

In various embodiments, a known data transmission standard is used for the data transmission, for example, Bluetooth, WLAN (WiFi), NFC or the like. In various embodiments, the hair treatment device or the hair treatment system has a corresponding data transmission device for transmitting and/or receiving the data.

In various embodiments, data collected by the hair treatment device (that is, the determined at least one sensor value and/or based on data and/or recommendations and/or a control or regulation parameter determined thereon) is provided.

In various embodiments, the analysis is performed by the hair treatment device itself, for example, by the circuit device, and an analysis result can be transmitted to a display device, for example, a display, a speaker, a smartphone, or the like, to provide the analysis result.

In various embodiments, the data is transmitted to/on an external data processing device (also referred to as an external platform), for example, on a smartphone with app, on a cloud, etc. After the data transmission to the external data processing device, the examination of the data can be executed by this, for example, to determine a control and/or regulation parameter and/or a recommendation.

In various embodiments, a matching of the cosmetic treatment with individualized consumer data facilitates an iterative cosmetic treatment cycle, improves an outcome of the cosmetic treatment, and/or increases a user's motivation to continue the treatment.

In various embodiments, a user is provided with information about a status of the hair (also referred to as a hair condition), which can further be used to determine an individual control or regulation of the hair treatment device and/or recommendation adapted to the hair condition of the user, for example, a product recommendation (for example, for a hair care and/or a hair styling product and/or a hair dyeing product) and/or a care recommendation, for example, a care recommendation, which concerns the hair of the user.

In various embodiments, a hair dyeing product is excluded from the hair treatment agents to be used.

In various embodiments, the control or regulation parameter or the recommendation is determined directly by the hair treatment device, that is, the electronic circuit device can be configured to determine the control/regulation parameter or the recommendation itself (also referred to as direct). For example, the electronic circuit device can be or have a data processing device, for example, it can be equipped with a memory and a processor, for example, a microprocessor, which can be configured, for example, by programming, to receive the sensor data and either provide it directly to the user, or to use the sensor data to provide the recommendation. For example, the sensor data can be compared with a database, which can have been obtained empirically, for example. Recommendations can be assigned to a plurality of sensor data in the database.

In various embodiments, the electronic circuit device is configured to indirectly determine the control or regulation parameter of the recommendation, for example, product or treatment recommendation. For example, the electronic circuit device (for example, in addition to a memory and a processor, for example, a microprocessor) can be equipped with a data transfer device that can be configured to transmit the sensor data received by the electronic circuit device to an external data processing device, for example, a computer, for example, a cloud, by which, for example, as described above for determining the control or regulation parameter or the recommendation by the electronic circuit device, the control or regulation parameter or the recommendation can be determined in order to provide the control or regulation parameter or the recommendation, for example, by transmitting to a display device and/or by transmitting the recommendation back to the electronic circuit device (for example, by the data transmission device). In various embodiments, the data transmission takes place in several stages, for example, by first transmitting the sensor data from the circuit device to the display device (for example, a smartphone, a tablet or the like), and the display device transmits the sensor data to the external data processing device (for example, the cloud).

In various embodiments, providing the control or regulation parameter or recommendation can have an adjusting of control or regulation parameters in the device to be controlled or regulated (for example, heatable part of the device, pump of a dispensing device, or the like), and/or a providing by transmitting the recommendation to a display device and displaying the recommendation.

The transmission can be done in various embodiments by a wireless transmission device. The wireless transmission device can be part of the electronic circuit device, for example. The wireless transmission device, in various embodiments, has a chip or tag that enables the wireless data transmission, for example, by Bluetooth, WLAN (WiFi), Zigbee, NFC, Wibree, Thread, WiMAX or the like.

In various embodiments, the display device has a computer screen, a smartphone, a tablet, an iPad, a smart mirror, a smartwatch, a laptop, or the like.

In various embodiments, a hair treatment device is provided. The hair treatment device can have a device body, at least one sensor for detecting a hair condition parameter arranged in or on the device body, and an electronic circuit device arranged in or on the device body, wherein the electronic circuit device can be coupled to the at least one sensor for detecting a hair condition parameter to receive the detected hair condition parameter, and wherein the electronic circuit device can be further configured, based on the received detected hair condition parameter, to control at least one hair treatment parameter and/or to dose at least one hair treatment agent and/or to provide a hair treatment recommendation.

The hair treatment device has a hair straightening iron in various embodiments.

In various embodiments, the controlled hair treatment parameter has a temperature of the hair treatment device.

In various embodiments, the at least one sensor for detecting a hair condition parameter is configured to be brought into contact with the hair of the user during the detection of the at least one hair condition parameter.

In various embodiments, the electronic circuit device further is configured to determine a hair condition information item and/or a recommendation based on the received sensor value and to provide it to the user.

In various embodiments, the recommendation has at least one recommendation selected from the group including hair care product recommendations, hair styling product recommendations and hair treatment recommendation.

In various embodiments, the at least one sensor is arranged sealed in the device body.

In various embodiments, the electronic circuit device has a wireless data exchange device.

In various embodiments, the sensor for detecting a hair condition parameter has at least one sensor selected from a group of sensors, the group of sensors having: a camera for recording a digital image of the hair, a temperature sensor, a moisture sensor, a microphone and a tensile force gauge.

In various embodiments, a hair treatment system is provided. The hair treatment system has a hair treatment device according to various embodiments and a display device, wherein the at least one hair treatment device can be configured to transmit to the display device the hair condition information item and/or the recommendation by the data exchange device.

In various embodiments, the display device has a computer screen, a smartphone, a tablet, an iPad, a smart mirror, a smartwatch or a laptop.

In various embodiments, a hair treatment system is provided. The hair treatment system has a device body, at least one sensor arranged in or on the device body for detecting a hair condition parameter, an electronic circuit device having a wireless data exchange device and a data processing device arranged in or on the device body, wherein the electronic circuit device can be coupled to the at least one sensor for receiving the detected electronic hair condition parameter, wherein the electronic circuit device can further be configured to transmit the received hair condition parameter to the data processing device by the wireless data exchange device, wherein the data processing device can be configured, based on the received detected hair condition parameter, to determine a control of a hair treatment parameter, and/or a dosage of a hair treatment agent and to transmit to the electronic circuit device or a further electronic circuit device arranged in a treatment device by the wireless data exchange device, and wherein the electronic circuit device or the further electronic circuit device can further be configured to control the at least one hair treatment parameter and/or to dose the at least one hair treatment agent.

In various embodiments, the data processing device has a smartphone, an iPad or a tablet.

In various embodiments, a method of providing cosmetic treatment of hair of the user is provided. The method includes, during a treatment and/or before a treatment of the hair by a hair treatment device according to various embodiments or by a hair treatment system according to various embodiments, detecting a hair condition parameter by the at least one sensor and controlling at least one hair treatment parameter and/or dosing at least one hair treatment agent and/or recommending at least one hair treatment based on the at least one hair condition parameter.

In various embodiments, the hair treatment parameter has a temperature of the hair treatment device.

The hair treatment device has a hair straightening iron in various embodiments. In various embodiments, the method further includes transmitting the detected hair condition parameter to the data processing device, and receiving the information provided by the external data processing device, wherein the determination of the at least one hair treatment parameter and/or the hair treatment agent dosage can be made based on the at least one hair condition parameter by the data processing device.

In various embodiments, the external computing device has or is a cloud.

In the following detailed description, reference is made to the accompanying drawings in which is shown by way of illustration specific embodiments. In this regard, directional terminology such as "top", "bottom", "front", "back", "front", "rear", etc. is used with reference to the orientation of the described figure(s). Since components of embodiments can be positioned in a number of different orientations, the directional terminology is illustrative and is in no way limiting. It should be understood that other embodiments can be utilized and structural or logical changes can be made without departing from the scope of the present disclosure. It should be understood that the features of the various embodiments described herein can be combined with each other unless specifically stated otherwise. The following detailed description is therefore not to be taken in a limiting sense, and the scope of the present disclosure is defined by the appended claims.

Figure 2A:
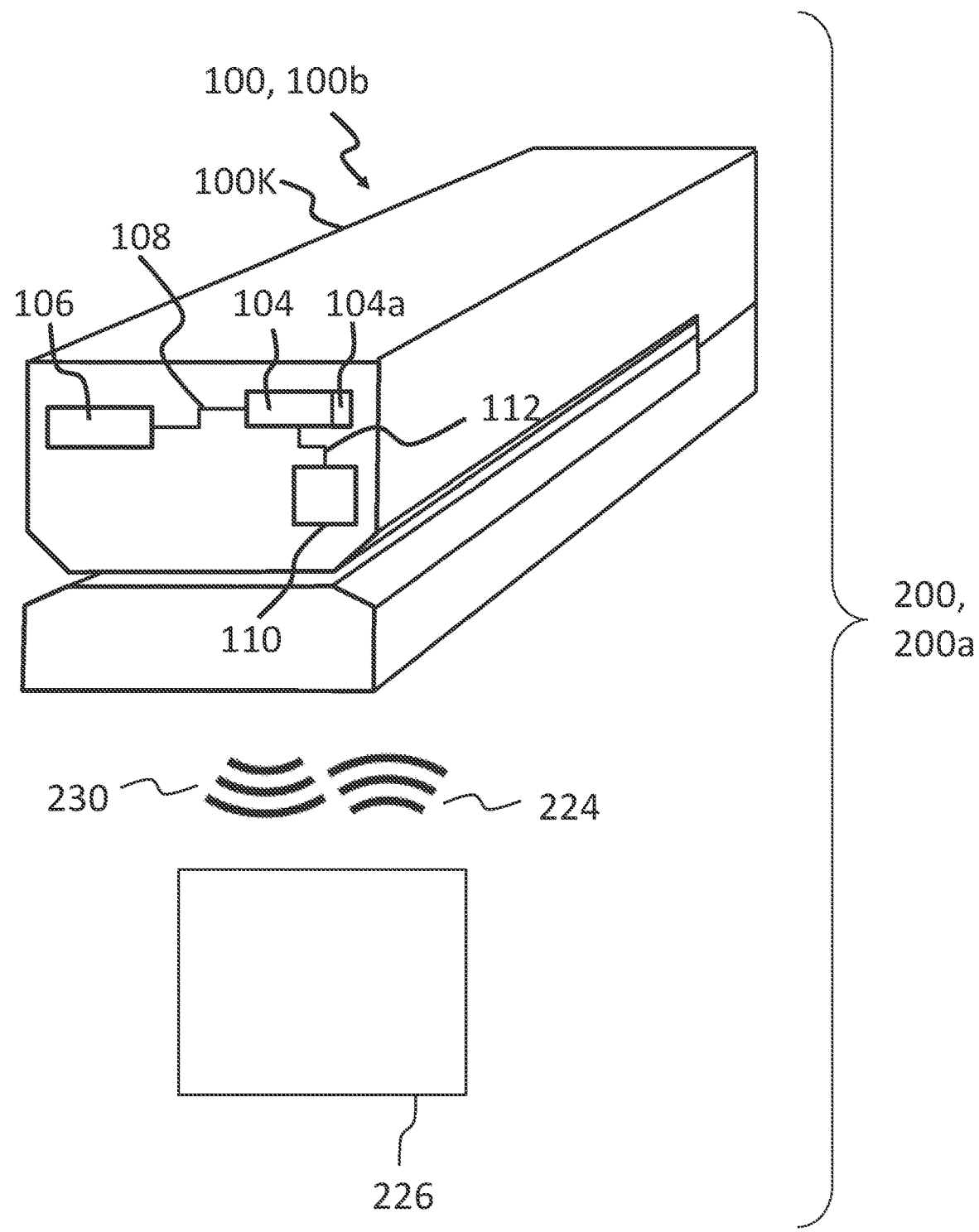
FIGS. 2A to 2C each illustrate a schematic representation of a hair treatment system according to various embodiments.
Figure 2B:
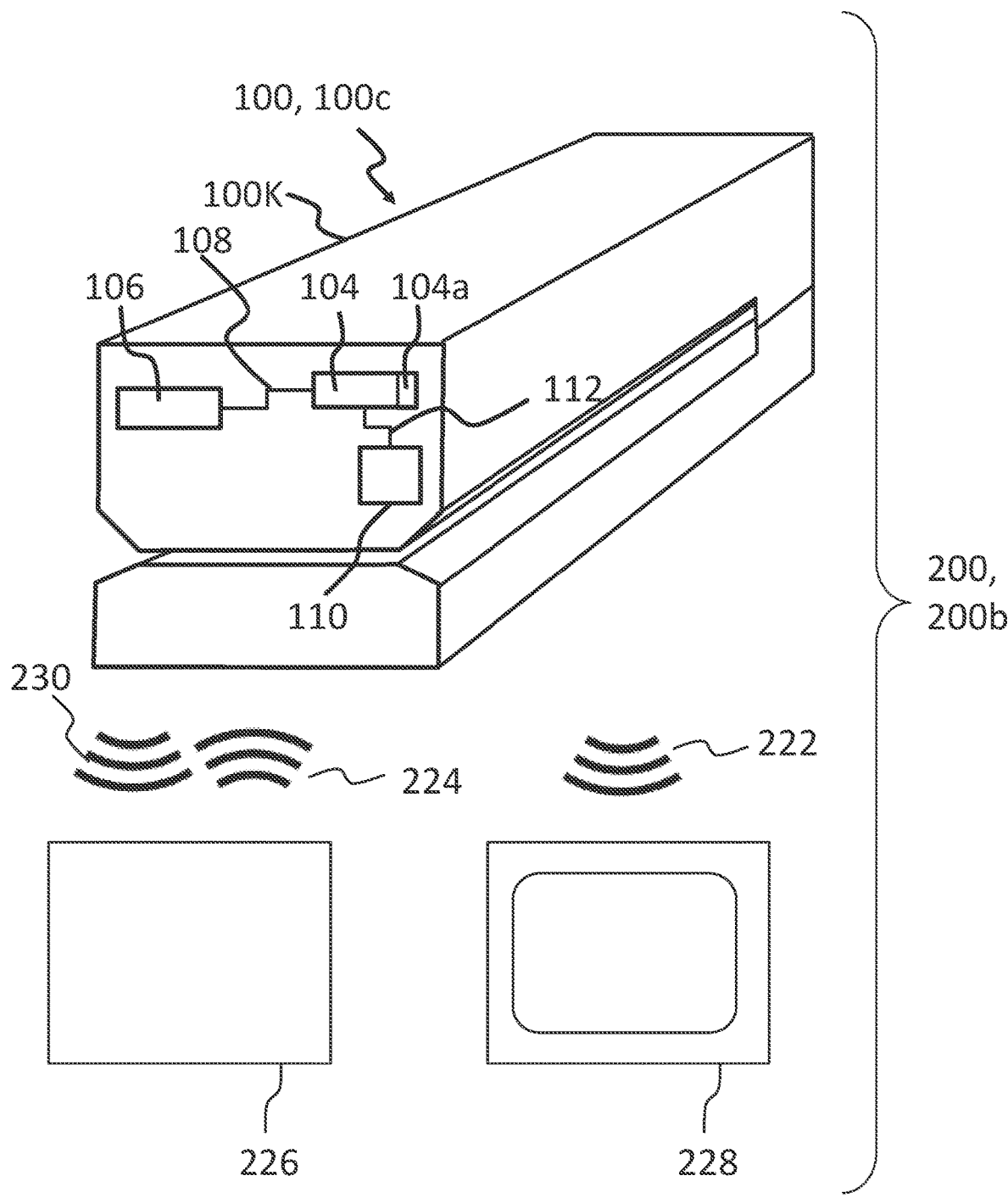
Figure 2C:
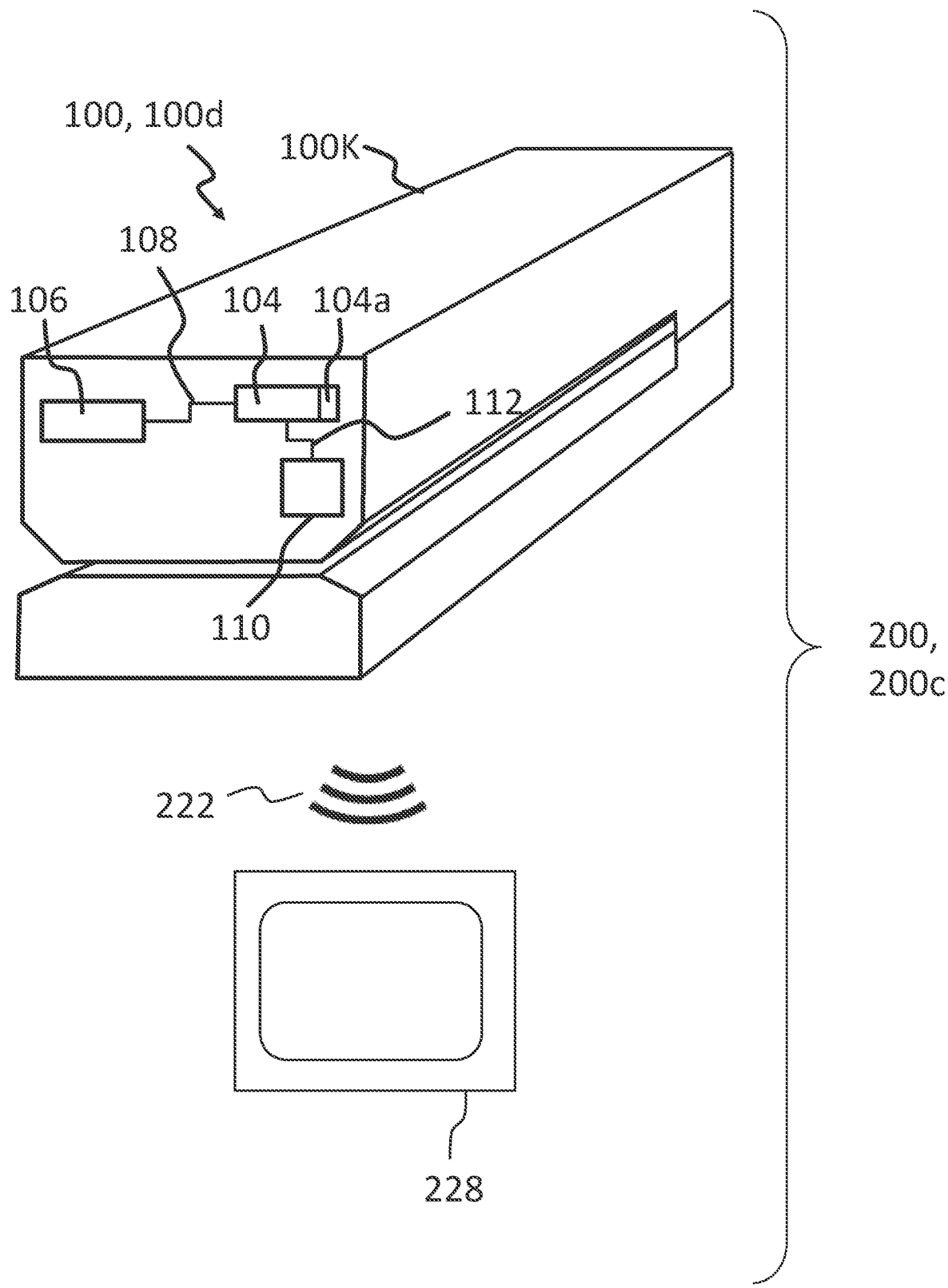
Figure 3:
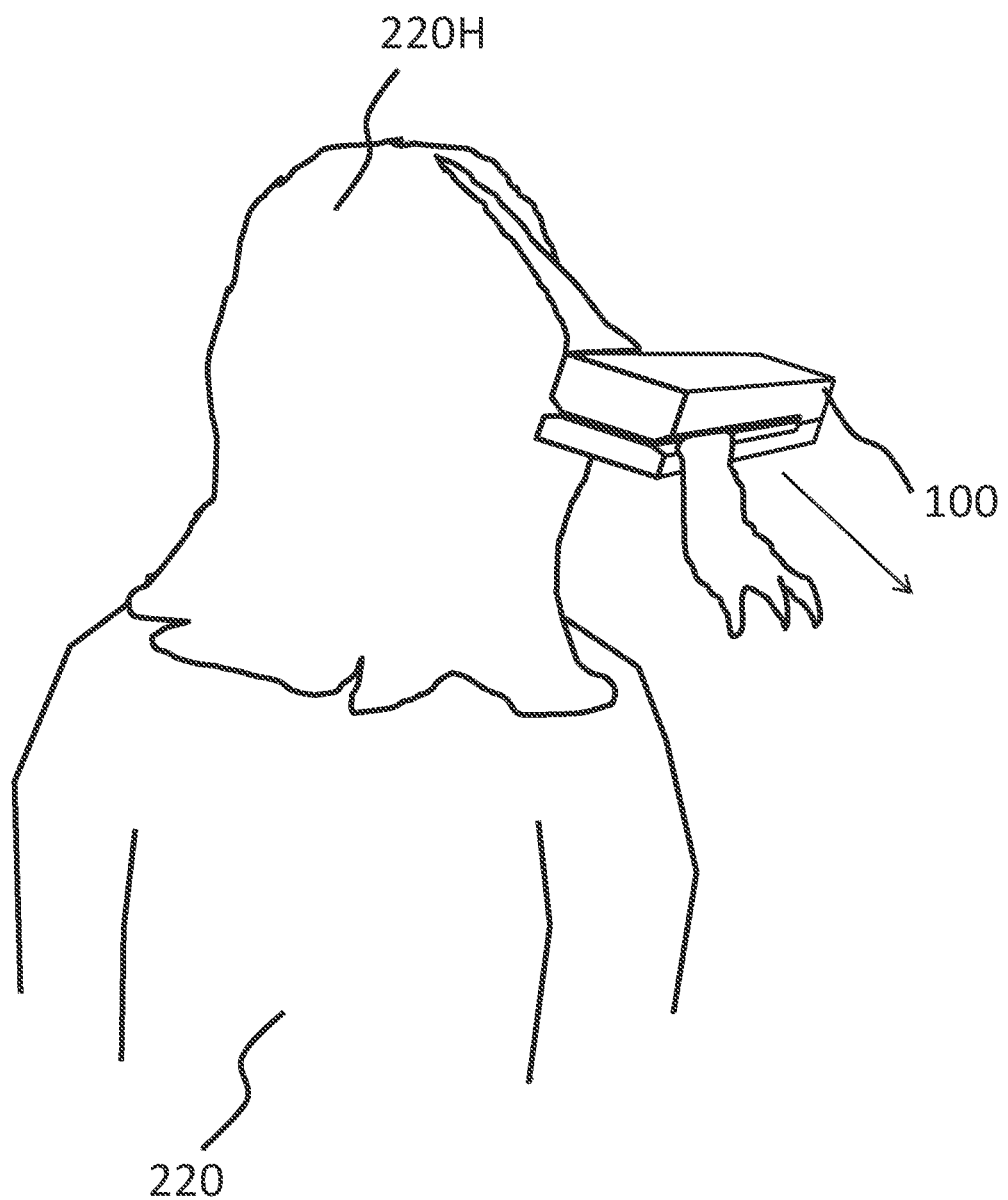
FIG. 3 illustrates a schematic representation of an application of a hair treatment device according to various embodiments.

FIG. 1 shows a schematic representation of a hair treatment system 100 according to various embodiments, FIG. 2A to FIG. 2C each show a schematic representation of a hair treatment system 200 according to various embodiments, and FIG. 3 illustrates a schematic representation of an application of a hair treatment system 200 according to various embodiments.

In various embodiments, a hair treatment device 100 is provided (various embodiments are identified as 100a, 100b, etc. respectively).

Although the hair treatment device 100 is shown schematically in the figures as a straightening iron, it should be understood that the hair treatment device can be of another type, for example, as described above. For example, the hair treatment device can have a curling iron, a comb, a brush, a drying hood or the like. If applicable, it should be understood that the embodiments in connection with the figures are also to apply to such types of hair treatment devices.

In various embodiments, the hair treatment device 100 has a device body 100K. The device body 100K can be formed of or have a solid material, for example, plastic or metal. For example, the device body 100K can be formed of a material or have a material commonly used for a straightening iron, a comb, a brush, or the like.

In various embodiments, in particular when the hair treatment device 100, 100a has a device for semi-permanent or temporary hair forming, for example, the straightening iron, the curling iron or the drying hood, the hair treatment device 100, 100a can further have a controllable or regulatable heating device (not shown), which can, for example, be integrated into the device body 100K.

In various embodiments, the hair treatment device 100 has at least two sensors 106 arranged in or on the device body. A sensor is used for detecting at least one hair condition parameter, and comprises, for example, a hair condition parameter as set forth above, for example, a hair moisture sensor, a sensor for degree of hair damage, a hair thickness sensor, a gray component sensor, a hair density sensor, a curl sensor, or the like. The second sensor is used to detect movements and location changes and in particular comprises a gyroscope.

In various embodiments, the at least one sensor for detecting a hair condition parameter is configured to detect more than one parameter, for example, the sensor can have an NIR spectrometer that can be configured to detect both parameters for determining hair moisture and parameters for determining degree of hair damage, and/or the sensor for detecting a hair condition parameter can have a camera, which can be configured to determine both parameters for determining the curl and parameters for determining the gray component.

In various embodiments, the at least two sensors 106 are incorporated in the device body 100K, for example, incorporated sealed. Thus, the hair treatment device 100 can be enabled to be insensitive to moisture and dirt. For example, the sealing can provide such that the hair treatment device can be cleaned without damaging the sensors 106 or another device. For example, the sensors 106 can be molded in, for example, during injection molding of the device body 100K.

In various embodiments, for example, when the at least two sensors 106 have an optical sensor, the device body 100K are transparent between the optical sensor and a surface of the device body 100K. In various embodiments, if it serves a purpose, the sensors 106 can be arranged in the device body 100 so as to face the hair 220H of the user 220 in a conventional arrangement of the hair on or in the hair treatment device 100 or are in contact with the hair 220H.

In various embodiments, the hair treatment device has an electronic circuit device 104 arranged in or on the device body 100K.

The electronic circuit device 104, in various embodiments, is coupled to the at least two sensors 106, for example, by a connection 108, for receiving the detected sensor value. The circuit device 104 can have its own coupling to each of the sensors 106. The coupling can, in various embodiments, have or be an electrically conductive connection, a (glass) fiber connection and/or a wireless connection. The electronic circuit device 104 can be configured to receive the at least two sensor values from the at least two sensors 106.

In various embodiments, the electronic circuit device 104 is or has a data processing device, for example, it can be equipped with a memory and a processor, for example, a microprocessor, which can be configured, for example, by programming, to receive the data from the sensors 106 and either directly control or regulate a hair treatment parameter, or to use the sensor data to provide a recommendation to the user 220.

The electronic circuit device 104 is configured in various embodiments to determine at least one recommendation based on the received data from the sensors 106 and to provide it to the user 220.

In various embodiments, the hair treatment device further has a controllable or regulatable actuator 110. The actuator 110 can be configured to influence a hair treatment parameter. A control or regulation of the actuator 110 is done in various embodiments by the electronic circuit device 104. The actuator 110 is connected to the electronic circuit device 104 by a connection 112 in various embodiments. The connection 112, in various embodiments, has or is an electrically conductive connection, a (glass) fiber connection and/or a wireless connection.

In various embodiments, the actuator 110 has temperature control or regulation of a heatable part of the hair treatment device 100.

In various embodiments, for example, in a case where the at least two sensors 106 are used, among other things, to determine a degree of hair damage, a curl, or the like, the hair treatment device 100 is configured to control the actuator 110, for example, to set a temperature corresponding to the degree of hair damage, the curl or the like for the hair treatment, for example, a straightening process or a curling process.

In various embodiments, for example, in a case where the at least two sensors 106 are additionally used, for example, to determine a hair temperature, for example, at positions in front of and behind the heating device, the hair treatment device 100 is configured to regulate the actuator 110, for example, a temperature for the hair treatment corresponding to the degree of hair damage, the curl or the like, for example, to adjust a straightening process or a curling process and to readjust based on the detected temperature (for example, in particular the temperature behind the heating device, that is, after the heat treatment).

In various embodiments, the hair treatment device 100 is configured to regulate the actuator 110 based solely on temperature sensor data.

In various embodiments, for example, in the case of a straightening iron or a curling iron, the actuator 110 is configured to be adjusted to a relatively high temperature, for example, in a range of from about 200° C. to about 230° C., if it is determined that, for example, the hair 220H of the user 220 is undamaged and/or thick, and adjusted to a relatively low temperature, for example, in a range of from about 150° C. to about 180° C., when it is determined that the hair 220H of the user 220, for example, is pre-damaged and/or thin.

In various embodiments, the user 220 also is provided with a hair treatment recommendation, for example, in the case of the straightening or curling iron, a recommendation "to treat each strand of hair for a maximum of five seconds" or the like.

In various embodiments, the actuator 110, for example, as an alternative or in addition to the temperature control or regulation, has a regulatable dispensing device (also referred to as a dosing device) that can be configured to dose a hair treatment agent based on the detected sensor data.

As stated above, the dispensing device can have at least one pump and/or at least one valve, which can be controllable or regulatable such that a volume or a quantity of the hair treatment agent can be dosed. In various embodiments, the dosing is done depending on a position of the hair treatment device 100 on the hair 220H, for example, upon determining that the hair treatment device 100 is located at the hairline, a different amount of the hair treatment agent can be delivered compared with a determination that the hair treatment device 100 is located at the hair tips. For example, the hair tips can require a greater amount of hair care agent than the hairline, while it can be the other way around with a hair coloring agent.

In various embodiments, as shown in FIG. 2A, a hair treatment system 200, 200*a* is provided.

The hair treatment system 200, 200*a*, in various embodiments, has a hair treatment device 100, 100*b*, which can be similar or identical in essential parts to the hair treatment device 100*a*.

The hair treatment device 100, 100*b* further has, in various embodiments, a data exchange device 104*a*, which can be configured to wirelessly transmit and receive data.

The hair treatment system 200, 200*a* further has, in various embodiments, an external data processing device 226, which, for example, can be part of a smartphone, a tablet, or the like, or a cloud, for example.

As described above, the data processing device 226 can be configured to receive the detected sensor data from the hair treatment device 100*b*, to determine the control or regulation parameters and/or the at least one recommendation, and/or to determine the speed and to transmit them to the hair treatment device 100*b*. That is, the hair treatment device 200*b* can be configured, as described above, to indirectly determine the control or regulation parameters and/or the at least one recommendation and/or the speed.

In various embodiments, as shown in FIG. 2B, a hair treatment system 200, 200*b* is provided.

The hair treatment system 200, 200*b*, in various embodiments, has a hair treatment device 100, 100*c*, which can be similar or identical in essential parts to the hair treatment device 100*a* and/or the hair treatment device 100*b*.

The data exchange device 104*a* of the hair treatment device 100, 100*c* can be configured in different embodiments to wirelessly transmit and receive data.

The hair treatment system 200, 200*b* further has a display device 228 in various embodiments.

As described above, the data processing device 226 can be configured to receive the detected sensor data from the hair treatment device 100*c*, to determine the control or regulation parameters and/or the at least one recommendation and/or the speed and to transmit them to the hair treatment device 100*c*. That is, the hair treatment device can be configured, as described above, to indirectly determine the control or regulation parameters and/or the at least one recommendation and/or the speed.

The display device 228 is configured in various embodiments to receive data from the hair treatment device 100*c*, for example, a recommendation determined by the electronic circuit device 104 and/or the external data processing device 226, for example, a hair treatment recommendation and/or a recommended hair care agent. The display device 228 can also receive data regarding the spatial location of the hair treatment device 100*c* and/or data regarding already treated hair regions from the hair treatment device 100*c*.

In various embodiments, as shown in FIG. 2C, a hair treatment system 200, 200*c* is provided.

The hair treatment system 200, 200*c*, in various embodiments, has a hair treatment device 100, 100*d*, which can be similar or identical in essential parts to the hair treatment device 100*a* and/or the hair treatment device 100*b* and/or the hair treatment device 100*c*.

The data exchange device 104*a* of the hair treatment device 100, 100*d* can be configured in different embodiments to wirelessly transmit and receive data.

The hair treatment system 200, 200*c* has a display device 228 in various embodiments.

The display device 228 is configured in various embodiments to receive data from the hair treatment device 100*d*, for example, a recommendation determined by the electronic circuit device 104, for example, a hair treatment recommendation and/or a recommended hair care agent or, by the electronic circuit device 104, determined data relating to the spatial position of the hair treatment device 100*d*.

In various embodiments, to determine a hair condition, for example, a degree of hair damage or the like, a database is used, as described above, in which the sensor data or possibly combinations of sensor data, the hair conditions (for example, degrees of hair damage) is assigned. The database can have been previously created by experiments, and/or can be continually created or supplemented by user data, for example, when using a cloud.

In various embodiments, the database further provides a product recommendation based on the hair condition, for example, degree of hair damage.

As shown in the following table, for example, at least one product recommendation (or also a styling or other hair treatment recommendation) can be assigned to the degree of hair damage in the database.

| Degree of hair damage | Product recommendation |
| --- | --- |
| very low | Product having very little care content |
| low | Product having little care content |
| medium | Product having medium care content |
| strong | Product having high care content |
| very strong | Product having very high care content |

The detected (measured) sensor values can, as described above, either be evaluated directly in the hair treatment device 100, for example, by the electronic circuit device 104, or indirectly evaluated by being transmitted to an external data processing device 226 to be evaluated there, for example, as described above. In this case, the sensor data or parts of the sensor data is evaluated in various embodiments by a comparison with (for example, empirically obtained) database entries.

In various embodiments, a determined hair condition (for example, degree of hair damage) is included in determining a recommendation, for example, a product or treatment recommendation.

In various embodiments, the determined hair treatment agent, for example, hair care agent, is applied to the hair by the hair treatment device or the hair treatment system, wherein control or regulation parameters for dosing the hair treatment agent by the electronic circuit device 104, the electronic circuit device 104*a* and/or the external data processing device 226 can be provided.

FIG. 3 shows a schematic representation of an application of a hair treatment device 100 according to various embodiments.

As shown in FIG. 3, the hair treatment device 100 can be used in a manner usual for the hair treatment device for hair treatment. A straightening iron is shown, in which the hairs 220H are pinched in strands and which is typically moved in the arrow direction, that is, in the direction from the hairline towards the hair tips. Analogously, for example, when using a curling iron as a hair treatment device, the hair is wound up by strands on the hair treatment device 100, the hair is combed through by strands when using a comb as a hair treatment device, etc.

Programming, for example, software, is used in various embodiments for the determinations described above. In this case, any software that provides a functionality described above can be used. In various embodiments, for example, in a case that a smartphone, a tablet or the like is used to carry out the method for the cosmetic treatment of hair of a user, the software is provided as an app.

In various embodiments, the circuit device integrated into the hair treatment device and/or an external data processing device, for example, a smartphone, a tablet, a laptop, a smart mirror, a smartwatch, an iPad, or the like, is suitable in order to be used when carrying out the method of providing a hair condition information item, for example, in determination operations, for example, by comparing with a database/reference values or the like. In various embodiments, the programming/software does not need to be provided on the smartphone, tablet, laptop, etc. For example, it can be sufficient when the circuit device integrated into the hair treatment device and/or the smartphone or the like is connected through the Internet, by means of WLAN or in another common way to a (for example, a further) external data processing device, for example, a computer, for example, a cloud. In such a case, the calculations can be carried out, for example, by the (further) external data processing device, for example, by the computer, and the result can be provided to the smartphone/tablet or the like and/or the internal circuit device.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair treatment device comprising:
   a device body;
   a first sensor arranged in or on the device body, the first sensor configured to detect a hair condition parameter;
   a second sensor arranged in or on the device body, the second sensor configured to detect movements and location changes of the device body; and
   an electronic circuit device arranged in or on the device body,
      wherein the electronic circuit device is coupled to receive the detected hair condition parameter from the first sensor and the detected movements and location changes from the second sensor,
      wherein the electronic circuit device is configured to control a hair treatment parameter and to dose a hair treatment agent based on the received detected hair condition parameter, and
      wherein the electronic circuit device is further configured to (i) determine a spatial position of the device body and a speed of the device body based on the received movements and location changes of the device body, (ii) determine, based on the determined spatial position of the device body, which hair regions have already been treated with the hair treatment device, and (iii) transmit data indicative of the hair regions that have already been treated; and
   a display device in operable communication with the electronic circuit, the display device configured to receive the data transmitted by the electronic circuit and, in response to receiving the data, to display at least the hair regions that have already been treated.

2. The hair treatment device according to claim 1, wherein the hair treatment device comprises a straightening iron.

3. The hair treatment device according to claim 1, wherein the electronic circuit device is further configured to determine whether the determined speed of the device body meets a predetermined criterion according to a provided speed for applying the hair treatment device.

4. The hair treatment device according to claim 3, wherein the electronic circuit device is further configured to deliver a signal depending on whether the determined speed meets the predetermined criterion.

5. The hair treatment device according to claim 4, wherein the signal comprises an acoustic signal, an optical signal and/or a haptic signal.

6. The hair treatment device according to claim 4, wherein the delivery of the signal occurs during application of the hair treatment device.

7. The hair treatment device according to claim 1, wherein the first sensor and the second sensor are sealed in the device body.

8. The hair treatment device according to claim 1, wherein the electronic circuit device comprises a wireless data exchange device.

9. The hair treatment device according to claim 1, wherein the second sensor is selected from the group of magnetic field sensors, gyroscopes, acceleration sensors, and mechanical displacement sensors.

10. A hair treatment system comprising:
   a hair treatment device comprising:
      a device body;
      a first sensor arranged in or on the device body, the first sensor configured to detect a hair condition parameter;
      a second sensor arranged in or on the device body, the second sensor configured to detect movements and location changes of the device body; and
      an electronic circuit device arranged in or on the device body, wherein the electronic circuit device is coupled to receive and transmit the detected hair condition parameter from the first sensor and the detected movements and location changes from the second sensor, and
   an external data processing device coupled to receive the detected hair condition parameter and the detected movements and location changes transmitted from the electronic circuit, the external data processing device configured, based on the detected hair condition parameter, to determine the control or regulation of a detected hair treatment parameter, determine a dosing for a hair treatment agent, and determine a speed at which hair treatment is to be performed, the external data processing device further configured to transmit the determined control or regulation, the determined dosing, and the determined speed to the electronic circuit device,
   wherein the electronic circuit device is configured to control a hair treatment parameter and to dose a hair treatment agent based on the determined control or regulation, the determined dosing, and the determined speed transmitted thereto from the external data processing device.

11. The hair treatment system according to claim 10, further comprising an actuator that is in electrical communication with the electronic circuit device and is configured to set a temperature of the device body based upon a hair condition parameter received from the electronic circuit device.

12. The hair treatment system according to claim 10, further comprising an actuator that is in electrical communication with the electronic circuit device and comprises a dispensing device that is configured to dose a hair treatment agent based upon the determined dosing.

13. The hair treatment system according to claim 10, further comprising a display device in electrical communication with the electronic circuit device.

14. The hair treatment system according to claim 10, wherein the hair treatment device further comprises a heating device that is interposed between the first sensor and the second sensor in or on the device body.

15. The hair treatment system according to claim 10, wherein the external data processing device is part of a smartphone, electronic or mobile tablet, personal computer, or a cloud-based server.

16. The hair treatment system according to claim 10, wherein the external data processing device comprises a database of product recommendations based on hair condition.

17. The hair treatment system according to claim 10, wherein the first sensor is selected from the group of a near-infrared spectroscope, a hair length sensor, an ultrasonic sensor, a photosensor, a thermal sensor, a spectrometer, and a camera.

18. The hair treatment system according to claim 10, wherein the device body comprises a heating device and wherein the external data processing device is further configured to determine the control or regulation of a temperature of the heating device based on the detected hair condition parameter and transmit the determined control or regulation of the temperature of the heating device to the electronic circuit device.

19. The hair treatment device according to claim 1, wherein the electronic circuit device is further configured to provide a hair treatment recommendation.

\* \* \* \* \*